(12) United States Patent
Martin

(10) Patent No.: US 6,602,516 B1
(45) Date of Patent: Aug. 5, 2003

(54) ANTIBIOTIC/MEDICATED GUTTA PERCHA POINT

(76) Inventor: Howard Martin, 11500 W. Hill Dr., Rockville, MD (US) 20852

( * ) Notice: Subject to any disclaimer, the term of this patent is extended or adjusted under 35 U.S.C. 154(b) by 0 days.

(21) Appl. No.: 09/674,636

(22) PCT Filed: May 5, 1998

(86) PCT No.: PCT/US98/09168

§ 371 (c)(1),
(2), (4) Date: Nov. 2, 2000

(87) PCT Pub. No.: WO99/56701

PCT Pub. Date: Nov. 11, 1999

(65) Prior Publication Data (65)

(51) Int. Cl.⁷ ............................ A61F 13/00; A61K 9/14; A01N 59/22; A01N 37/18; A01N 31/65; A61C 5/04
(52) U.S. Cl. .................. 424/422; 424/485; 424/667; 433/226; 514/152; 514/154
(58) Field of Search ................... 424/422, 423, 424/485, 667; 433/226; 514/152, 154

(56) References Cited

U.S. PATENT DOCUMENTS

| | | | | |
|---|---|---|---|---|
| 4,483,679 A | * | 11/1984 | Fujisawa et al. | 433/228 |
| 4,657,592 A | * | 4/1987 | Takubo | 106/35 |
| 4,931,096 A | * | 6/1990 | Fujisawa et al. | 106/35 |
| 5,023,082 A | * | 6/1991 | Friedman et al. | 424/426 |
| 5,380,530 A | * | 1/1995 | Hill | 424/440 |
| 5,447,725 A | * | 9/1995 | Damani et al. | 424/435 |
| 5,646,197 A | * | 7/1997 | Martin | 523/118 |
| 5,648,403 A | * | 7/1997 | Martin | 523/117 |
| 5,783,205 A | * | 7/1998 | Berggren et al. | 424/426 |

\* cited by examiner

*Primary Examiner*—Sreeni Padmanabhan
*Assistant Examiner*—Lauren Q. Wells
(74) *Attorney, Agent, or Firm*—Law Offices of Royal W. Craig

(57) ABSTRACT

The ability to incorporate iodoform, tetracycline and a combination of iodoform/tetracycline into root canal gutta percha points is described. The iodoform, tetracycline and iodoform/tetracycline combination are bound within the gutta percha points. They act as a reservoir of antimicrobial that is capable of diffusing onto the surface of the gutta percha thereby inhibiting the colonization of bacteria on the gutta percha points and within the root canal system. Tetracycline is capable of coalescing within the dentinal tubules to inhibit long term microbial growth. These medicated gutta percha points are site specific, surface acting antimicrobial gutta percha points.

A method of the usage and delivery of amorphous form iodoform gutta percha, iodoform/tetracycline gutta percha, or tetracycline gutta percha within a heated compule with a pressure plunger by delivering the thermo-softened heat labile amorphous form via a pressure extrusion system through a cannula into the prepared root canal system.

7 Claims, 2 Drawing Sheets

ANTIBACTERIAL IODOFORM GUTTA PERCHA

| Microorganism | CONTROL GP | IODOFORM |
|---|---|---|
| Staphylococcus aureus | - | - |
| Escherichia Coli | - | - |
| Streptococcus mutans | - | - |
| Streptococcus sanguis | - | - |
| Actinmyces viscous | - | ++ |
| Eneterococci faecum | - | - |
| Prevotella intermedius | - | + |
| Veillonella parvula | - | ++ |
| Peptococcus niger | - | ++ |
| Porphyromonas gingivalis | - | ++ |

Code:
"-" = no visible zone of inhibition
"+" = <10mm clear zone or diffuse growth within zone
"++" = > 10mm clear inhibition zone

FIG. 1

ANTIBACTERIAL ACTIVITY TETRACYCLENE HCL GUTTA PERCHA

| MICROORGANISM | CONTROL GUTTA PERCHA (GP) | TETRA GP |
|---|---|---|
| Staphylococcus aureus | − | + |
| Streptococcus epidermius | − | ++ |
| Escherichia Coli | − | + |
| Actinomyces comitans | − | ++ |
| Proteus gingivalis | − | ++ |
| Proteus micros | − | + |

Code:
"−" = no visible zone of inhibition
"+" = <10mm clear zone or diffuse growth within zone
"++" = > 10mm clear inhibition zone

FIG. 2

ANTIBIOTIC/MEDICATED GUTTA PERCHA POINT

TECHNICAL FIELD

The present invention relates to antibacterial gutta percha for obturation of root canals and, more particularly, to an improved gutta percha point comprising tetracycline and/or iodoform and method for application of the same that yields a broader spectrum of effectiveness based upon the clinical symptomatology in combating the bacterial contamination of leakage and reinfection. The method for application allows the dentist to chose the properly medicated gutta percha point for the individual case.

BACKGROUND ART

The aim of endodontic treatment is the elimination of infection from the root canal and the prevention of reinfection within the root canal. Bacteria have long been recognized as the primary etiologic agent of reinfection within the root canal. Proper obturation of the root canal space is a key to this success.

According to the Washington University study nearly 60% of the failures studied occurred because of canal leakage. Salivary fluid, apical fluids, and leakage infiltration due to open lateral canals because of periodontal disease, all contribute to leakage failure and subsequent reinfection of the root canal.

Complete obturation of the root canal is impossible via the universally accepted solid core filling material gutta percha. The usual method of obturation with gutta percha is the lateral condensation technique. This is a compression of the solid gutta percha cones together and adaptation to the canal walls. Numerous studies show leakage alongside the gutta percha cones due to the mere lamination of the gutta percha cones rather than developing a homogenous mass. Even the warm vertical/lateral condensation technique will not give a complete adaptation to the canal walls as shown by several leakage studies, all of which require root canal sealer to attempt to fill in the remaining voids.

Loma Linda University (Torabinejad et al., J. Endo 1990, 16:12,566) has also shown that a significant problem in leakage has been through the coronal aspect of the root canal due to delay in placing a permanent restoration, breaking down of the temporary seal, partial fractures or a poorly placed permanent restoration. Over 50% of the root canals were contaminated within 19 days with *Streptococcus epidermidis* and *Proteus vulgaris*.

University of Iowa's Swanson and Madison (J. Endo, 1987 13:56) found, in their studies that in 82% of the cases, the entire root length was penetrated by bacteria, showing that traditional gutta percha was an inadequate seal.

An attendant problem within the root canal, is the polymicrobial aspect of the contamination. In a combined study, the University of Zurich and University of Umea, Sweden (Nair et al, J. Endo, 1990,16:580), showed that multiple bacterial species and two types of yeasts were found within the canals.

Fabricius' group extensive studies (Scand. J. Dent Res, 90:134,1982, Scand J. Dent Res, 1982,90: preprint, Scand J. Dent Res, 1982,90: preprint, Scand J Dent Res, 1981, B9:475) at University of Gothenburg, Sweden demonstrated that mixed infections of various bacterial strains were commonplace. His group found that anaerobic strains, especially Bacteroides species were present in longer standing infections and that aerobic or facultative anaerobic bacteria were more common in incipient or shorter to mid term infections.

In the apical region of the root canal, Fabricius found that the fastidious slow growing obligate anaerobic bacterial strains outnumbered the facultative strains. Therefore, bacteria after closure, activated due to leakage by the inadequate seal of gutta percha, will after a time period multiply and reinfect the root canal as they require little or no oxygen to survive and replicate.

Bacteria are also found to have penetrated the dentinal tubules during original infections and cannot be totally eliminated via biomechanical treatment procedures. These lyophilized bacteria will also become active during the leakage phase contributing to reinfection. The bacteria are of both types of Gram strain being positive and negative. However, Gram negative predominates within the canal and both cocci and rods of each type are found. The longer-standing the infection, the more Gram negative rods are found.

The obligate anaerobic portion of root canal infection has been linked to the acute exacerbation or flare up. This is characterized by swelling, pus, pain and bone destruction. This has been corroborated by the benchmark bacteroidies study (J. Endo 15:13,1989) done by Sunqvist at the University of Umea, Sweden. This knowledge has been developed with the advent of the ability now to culture obligate anaerobic Gram negative organisms, These were previously undetected due to lack of this capability in prior bacteriologic studies.

The dentist can now determine, based upon symptomology, bacteriologic studies statistics, and etiology, the most likely type of bacteria present. The dentist then can utilize the correct pharmacologic obturation materials for treatment and preservation of the root canal integrity.

Eguchi et al at the endodontic research clinic, US Army, Ft. Campbell, Ky. (J. Endo, 11:166, 1985) showed that no matter what technique was used with gutta percha for obturation, lateral, vertical heat, mechanical or chemical dip, the range of obturation sealing was 77–95%. This allows sufficient space for the breakdown and reinfection due to leakage contamination to occur, as well as failure due to poor fills, and failure due to inadequate cleaning and disinfection.

Gutta percha is the obturation material of choice. Its antibacterial properties are not significant in its traditional form. The present inventor has previously disclosed in U.S. Pat. No. 5,648,403, issued Jul. 15, 1997, that iodoform 10% in gutta percha has antibacterial properties superior to traditional gutta percha.

However, upon further testing, Iodoform has been shown to be ineffective against tested aerobes such as *Streptococcus mutans, Streptococcus sanguis, Escherchi coli, Staphylococcus aureus,* and the facultative anaerobe, *Enterococci faecium,* Actinomyces, Lactobacillus, *Prevotella intermedius*. This study was accomplished at the Naval Dental School, Bethesda, Md. and the results are as shown in FIG. 1. FIG. 1 indicates that the iodoform/gutta percha of Martin's previous formulation will not always be effective against all types of organisms but is effective against facultative gram – and gram + rods and cocci as well as obligate anaerobes. This shows that iodoform gutta percha is more effective against a longstanding infection of the root canal and against organisms present within the oral microbiota that have reduced oxygen potential. However, it is not as effective against an oral salivary leakage contamination as determined by the previous leakage and bacterial investigations.

It would be significantly advantageous to provide an alternative and combination gutta percha point and method for selection and application that has a broader spectrum of effectiveness based upon the clinical symptomatology, to thereby combat the bacterial contamination of leakage and reinfection.

DISCLOSURE OF INVENTION

According to the present invention, the above-described and other objects are accomplished by providing an improved gutta percha point comprising tetracycline and/or iodoform and method for application of the same that yields a broader spectrum of effectiveness based upon the clinical symptomatology in combating the bacterial contamination of leakage and reinfection. A method of preparation of a compule and delivery by a cannula is also disclosed that allows the dentist to select the properly medicated gutta percha point for the individual case.

BRIEF DESCRIPTION OF DRAWINGS

These and other advantages of the disclosed invention will become apparent from a reading of the following description when read in conjunction with the accompanying drawings in which:

FIG. 1 is a table illustrating the results from a study at Naval Dental School, Bethesda, Md., the iodoform/gutta percha disclosed in U.S. Pat. No. 5,648,403, issued Jul. 15, 1997. The results show that while iodoform 10% in gutta percha has antibacterial properties superior to traditional gutta percha, the combination will not always be effective against all types of organisms.

FIG. 2 is a table showing an in vitro study accomplished with tetracycline impregnated gutta percha points showing antimicrobial activity against a variety of specimens in an agar medium.

BEST MODE(S) FOR CARRYING OUT THE INVENTION

Gutta percha is a high molecular weight polymer trans polyiosprene. If it is heated above 650° C. it becomes amorphous. It is cooled at 0.50° C. per hour and will slowly recrystallize in the beta form which is the form of dental gutta percha usage. It is in the complex alpha and beta form that the dental gutta percha points are shaped. The gutta percha is amorphous when the zinc oxide, iodoform, tetracycline, dye, wax/resin are added. The baseplate gutta percha, a flat segment, is then cut into strips and either hand rolled or mechanically rolled into the predetermined gutta percha point sizes.

The antimicrobial chemicals, iodoform or tetracycline, that are utilized in the gutta percha point are incorporated into the form by a special warming process so as to be evenly distributed throughout the medicated gutta percha point. Iodoform of 99.5% purity must be used. All impurities are removed in creating the triodomethane. The tetracycline hydrochloride salt is the proper choice for incorporation into the gutta percha as is the other tetracycline family of products in the chloride salt the choice also. This is also processed to be 99.95% pure prior to insertion. Compression of the material is a factor and the material is mortared into the zinc oxide/gutta percha while still warm. The gutta percha, zinc oxide and antimicrobials, wax/resin must be thoroughly milled to insure complete dispersion throughout the gutta percha point.

It is the intention of the present application to improve upon the description of proper processing iodoform and the usage of iodoform in gutta percha points for specific organisms, the addition of the antibiotic tetracycline for other susceptible organisms, as well as creating a combination medicated gutta percha point for greater antibacterial spectrum usage.

The selection of tetracycline is predicated upon studies done that show that tetracycline will bind into bone and dentin within the root canal and will have little or no allergic reactions. The Boston Collaborative Drug Surveillance Program determined that tetracycline caused no allergic reactions in more than 1,000 patients. The tetracyclines are broad spectrum antibiotics and are effective against a wide variety of Gram positive and Gram negative organisms.

The in vitro study is shown in FIG. 2 was accomplished with tetracycline impregnated gutta percha points showing antimicrobial activity against a variety of specimens in an agar medium. The impregnated gutta percha produced significant zones of inhibition indicative of active tetracycline being leached from within the gutta percha point. The untreated gutta percha displayed no inhibition. All tetracyclines appear to have essentially the same potency against the same organisms. Bacterial resistance against tetracycline develops slowly and has not been a significant problem.

The important fact is that tetracyclines can become incorporated into calcified structures. This enables the tetracycline to leach out when contamination leakage occurs within the root canal. Tetracycline will become incorporated within the dentinal tubules where bacteria are and will inhibit the lyophilized bacteria thereby not allowing these bacteria to regenerate and cause canal reinfection. The tetracyline will also destroy and inhibit the bacteria that penetrate along the surface of the gutta percha points that have become contaminated due to apical, lateral or coronal microleakage after obturation.

Tetracycline is stable in an acid environment thereby making it effective in the inflamed area of the root canal periapex. Inflammation is an acidic environment that will neutralize most alkaline type antimicrobials. A distinct advantage for the tetracyclines. The hydrochloride salt of tetracycline is the form utilized. Tetracycline has a higher blood level concentration than others in the tetracycline family except for the doxycycline form. As noted, tetracycline can form a stable chelate complex with metallic ions such as calcium and magnesium thereby allowing the attachment to the dentinal wall within the root canal along which the leakage and contamination occurs.

The tetracycline is released in similar leaching fashion to iodoform impregnated gutta percha points. Tissue fluid or salivary contamination causes the tetracycline, or iodoform, or the combination of the two antimicrobials to diffuse from the gutta percha points into the external medium, the contaminated tissue fluid within the canal.

It is the ability of the tetracycline or iodoform to depress or suppress bacterial growth that results in maintaining the integrity of the root canal obturation. This has been shown to be accomplished in more open cases such as periodontal pocket disease by Tonetti et al (Int. J. Perio Rest Dent 14:421,1994).

However, Olsvik et al. (J. Clin. Perio. 22:391, 1995) has shown that anaerobic gram negative rods and Streptococcus spp. was resistant to tetracycline with an overall resistant rate of 23%. This demonstrates that tetracycline is not an all inclusive microbial inhibitor. It is therefore necessary to selectively combine the tetracycline with the iodoform to expand the spectrum of bacteriostasis or bacteriocidal effects within the failing root canal gutta percha.

The proper method of application of the optimum gutta percha point (inclusive of tetracycline and/or iodoforn) according to the present invention therefore calls for the administering dentist to evaluate the clinical symptoms and radiographs to determine which medicated form of gutta percha should be utilized for the obturation technique. The added advantage of tetracycline being able to coalesce within the canal wall is a distinct advantage for long standing root canal infections that would have bacterial penetration within the dentinal tubules. On the other hand, iodoformn gutta percha would be better for relative short term infected cases. In the case of swelling and purulence, a combination point of iodoform/tetracycline gutta percha would be the optimum choice.

In this latter case where a combination antimicrobial iodoform/tetracycline gutta percha point is selected, barium sulfate is removed completely, as the iodoform acts as the radioopacifier as well as an antimicrobial.

The optimum gutta percha point (inclusive of tetracycline and/or iodoform) according to the present invention may then be applied by the lateral condensation technique. This is a compression of solid gutta percha cones together and adaptation to the canal walls.

The proper gutta percha formulation for tetracycline and/or iodoform according to the present invention is as shown below:

| Tetracycline Gutta Percha point: | |
| --- | --- |
| Gutta Percha - | 20% |
| Zinc Oxide - | 57% |
| Barium Sulfate - | 10% |
| Beeswax - | 3% |
| Tetracycline HCl - | 10% |
| Combined Antimicrobial Gutta Percha point: | |
| Gutta Percha - | 20% |
| Zinc Oxide - | 57% |
| Triiodomethane (Iodoform) | 10% |
| Tetracycline HCl - | 10% |
| Beeswax - | 3% |

The preferred amounts of constituents as described above may vary by approximately 10% without significantly compromising effectiveness.

Another format of the usage and delivery of the above-described iodoform gutta percha, iodoform/tetracycline gutta percha, or tetracycline gutta percha is in the form of a heated compule with a pressure plunger delivering the thermo-softened material through a cannula into the prepared root canal system. For this, the iodoform gutta percha, tetracycline gutta percha, iodoform/tetracycline gutta percha is formed into a heat labile amorphous mass and is placed within a compule that when heated will be able to be expressed through a cannula into the root canal system as a back filling procedure technique. To prepare the amorphous form of the iodoform gutta percha, tetracycline gutta percha, or iodoform/tetracycline gutta percha, alpha phase gutta percha is impregnated with the iodoform, tetracycline or combination iodoform/tetracycline per the formulations described herein. The medicated gutta percha forms are milled under advancing heat to thin the viscosity. Approximately 10–15 minutes are required to fully plasticize the medicated gutta percha within the compule heater. The amorphous form is be sufficiently milled to plasticize at that temperature which takes longer and slower to achieve than the usual method described for normal incorporation of the aforementioned antimicrobials. This slower, longer process develops a lower melting point in the gutta percha, thereby enabling the flow phase when it is gently heated prior to the filling extrusion technique. The amorphous form is then placed in its amorphous state within a pre existing plastic compule. These compules are available from several dental manufacturers and have been utilized for various light cured restorative resin materials. These compules have a cannula attached for expressing the antibiotic or medicated gutta percha into the canal. The compules are heated by various conventional devices, thereby softening and thermoplasticizing the antiobiotic or medicated gutta percha. Any heat source that will reach 70° C. is to be utilized to thermoplasticize the gutta percha within the compule for dispensing, but the temperature of the heating device must not go over 175 degrees F. as the tetracycline or iodoform would be altered. It takes several minutes of heating the compule to enable the flowability so that proper extrusion of the antibiotic/medicated gutta percha will occur. Conventional compule syringes or compule guns are available for utilization as the pressure force for the extrusion phase.

A commercially available V-shaped pistol grip holder compule gun/syringe as utilized routinely in restorative dentistry can be used as the dispensing source. Ultrafil™ by Hygenic Corp has a system that uses a disposable cannula which can be heated in an oven to 70° C. The cannula is then placed in a modified ligamental syringe for injecting into the root canal. For the iodoform gutta percha, iodoform/tetracycline gutta percha or tetracycline gutta percha of the present invention, the cannula gauge must be no larger than 22 but preferably 25.

Therefore, the distinguishing factor is the new medicated forms of the gutta percha to be utilized in a heated compule so that the gutta percha softens and under pressure from the mechanical gun/syringe will flow out through the cannula into the root canal to obturate narrow areas, lateral canals, in the root canal system based upon its improved rheology. This method can also be used in a backfill system of the canal after a master gutta percha cone has been fitted.

The above-described method of delivery of the medicated gutta percha will enable a rapid obturation of the middle and cervical portion of the root canal.

What is of importance here is the fact of the site specificity and surface action of the iodoform and tetracycline effects as antimicrobials, the method of incorporation of the iodoform, tetracycline or iodoform/tetracycline into gutta percha and the processing of the same within the gutta percha point. As the studies have shown, iodoform gutta percha will work against certain aerobic bacteria, while it is most effective against obligate anaerobic and facultative anaerobic organisms of the long standing infections. The tetracycline gutta percha will work against oral contamination, periodontal contamination and aerobic and facultative anaerobic organisms while not as effective against long standing infection. The combination of tetracycline/iodoforn gutta percha is the most effective against a wide variety of gram positive and negative organisms as well as aerobic, facultative and obligate anaerobes.

Obviously, many modifications may be made without departing from the spirit of the present invention. Accordingly, it will be appreciated by those skilled in the art that within the scope of the appended claims, the invention may be practiced other than has been specifically described herein.

Industrial Applicability

Iodoform gutta percha is effective against a longstanding infection of the root canal and against organisms present within the oral microbiota that have reduced oxygen potential. However, it is not as effective against an oral salivary leakage contamination as determined by the previous leakage and bacterial investigations. There would be a significant advantage to providing an alternative and combination gutta percha point and method for selection and application that has a broader spectrum of effectiveness based upon the clinical symptomatology, to thereby combat the bacterial contamination of leakage and reinfection. It would also be advantageous to provide an improved method for preparing and delivering the above-described iodoform gutta percha, iodoform/tetracycline gutta percha, or tetracycline gutta percha in the form of a heated compule through a cannula into the prepared root canal system.

What is claimed is:

1. An antimicrobial gutta percha point for root canal obturation consisting of

Gutta Percha—20%;

Zinc Oxide—57%;

Triiodomethane—10%;

Tetracycline—10%; and

Beeswax—3%.

2. The antimicrobial gutta percha point for root canal obturation according to claim 1, wherein said tetracycline is selected from the group consisting of Tetracycline HCl, Tetracycline phosphate, Doxycycline hyclate, Minocycline HCl, Oxytetracycline HCl, Chlortetracycline HCl, and Demethylchlortetracycline HCl.

3. A formula for a tetracycline medicated gutta petcha point for root canal obturation consisting of:

Gutta Percha—20%;

Zinc Oxide—57%;

Tetracycline HCl—10%;

Barium sulfate—10%;

Beeswax—3%.

4. A process of incorporating tetracycline HCl into the gutta percha formulation of claim 3 comprising the steps of:

making Gutta Percha amorphous by melting above 65 C.;

cooling said Gutta Percha at 0.5 C. per hour;

combining zinc oxide, barium sulfate, beeswax, and tetracycline HCl by mixing, compressing, or mortaring;

milling the combination into a flat form, cutting into strips, and forming said strips into a gutta percha point having a tapered shape.

5. A method of administering the gutta percha formulation of claim 3 for root canal obturation, comprising the steps of:

combining zinc oxide, barium sulfate, beeswax, and tetracycline HCl;

placing said combination within a preformed compule;

heating said combination within said compule;

pressure-extruding said combination from said compule through a cannula into the root canal.

6. A process of incorporating triiodomethane and tetracycline into the gutta percha formulation of claim 1 comprising the steps of:

making Gutta Percha amorphous by melting about 65 C.;

cooling said Gutta Percha at 0.5 C. per hour;

combining zinc oxide, beeswax, triiodomethane, and tetracycline by mixing, compressing, or mortaring;

milling the combination into a flat form, cutting into strips, and forming said strips into a gutta percha point having a tapered shape.

7. A method of administering the gutta percha formulation of claim 1 for root canal obturation, comprising the steps of:

combining zinc oxide, beeswax, triiodomethane, and tetracycline;

placing said combination within a preformed compule;

heating said combination within said compule;

pressure-extruding said combination from said compule through a cannula into the root canal.

* * * * *